United States Patent [19]

Sanders

[11] Patent Number: 5,786,151
[45] Date of Patent: Jul. 28, 1998

[54] MICROENCAPSULATED LABELLING TECHNIQUE

[75] Inventor: Michael F. Sanders, Slough, Great Britain

[73] Assignee: The Minister of Agriculture Fisheries & Food in her Britannic Majesty's Government of the U.K. of Gt. Britain & N. Ireland

[21] Appl. No.: 849,407

[22] PCT Filed: Jun. 23, 1995

[86] PCT No.: PCT/GB95/01478

§ 371 Date: May 30, 1997

§ 102(e) Date: May 30, 1997

[87] PCT Pub. No.: WO96/01428

PCT Pub. Date: Jan. 18, 1996

[30] Foreign Application Priority Data

Jul. 1, 1994 [GB] United Kingdom ............... 9413308

[51] Int. Cl.$^6$ ............... C12Q 1/68; G01N 33/569; G01N 33/58; G01N 33/532

[52] U.S. Cl. ............... 435/6; 435/7.1; 435/7.2; 435/7.32; 435/7.72; 435/8; 436/501; 436/518; 436/829; 536/22.1; 530/391.3

[58] Field of Search ............... 435/6, 7.1, 7.2, 435/7.32, 7.72, 8; 436/501, 518, 829; 536/22.1; 530/391.3

[56] References Cited

U.S. PATENT DOCUMENTS 4,604,364  8/1986  Kosak ............... 436/501
4,704,355  11/1987  Bernstein ............... 435/6

FOREIGN PATENT DOCUMENTS

A 0256 373  2/1988  European Pat. Off. .
A 0 577 092  1/1994  European Pat. Off. .

*Primary Examiner*—Toni R. Scheiner
*Attorney, Agent, or Firm*—Nixon & Vanderhye

[57] ABSTRACT

Labelling techniques for specific binding agents are provided wherein the label used comprises a microcapsule containing a nucleotide, preferably in solid form and preferably in crystalline form. Preferred nucleotide is ATP. The presence of labelled agent is determined by disrupting the microcapsule and measuring the amount of nucleotide so released; that being related to the amount of binding agent and thus any related interaction with the target for that agent such as a specific DNA or microorganism.

27 Claims, No Drawings

MICROENCAPSULATED LABELLING TECHNIQUE

The present invention relates to a methods and apparatus for the detection, identification and/or quantification of materials that are capable of being bound by specific binding agent, particularly biological materials such as antigens, microorganisms and nucleic acids. Particularly the methods enable detection of low numbers of microorganisms of specific genus, species or serotype, in isolated form or as contaminants in foodstuff, environmental or forensic samples.

There are many requirements for methods of screening for specific substances in low quantity in specific environments, such as for microorganisms such as bacteria, for example, for the detection of human bacterial pathogens in contaminated foods. Public health and quality control bodies demand rapid bacterial detection methods which have suitable levels of specificity and sensitivity, but few satisfactory methods exist.

In recent years, food poisoning has become a major topic of both public and scientific debate. This has been of great concern to the food producing industries and has led to increased demands for rapid bacterial food screening procedures to ensure product quality and allow early release for sale. If pathogenic bacteria are present in commercially prepared products they are likely to occur in very low numbers and it is this fact which makes bacterial detection a slow process, often taking days to complete.

Current bacterial detection techniques need the presence of high numbers of bacterial cells ($10^5$–$10^8$) at the final stage before detection is possible. The increase in cell numbers is achieved by laborious and time consuming procedures involving selective enrichment and isolation steps.

U.S Pat. No. 4,704,355 (Bernstein) discloses the use of sensitised liposomes containing ATP which may be used in assays for antigens and DNA probes. Unfortunately, by their very nature, liposomes can only be used effectively to contain fluids and can not be isolated or stored in dry powder form. This can lead to problems with the stability and retention of the fluid and solute contained therein. Such problems are particularly common during even quite short periods of storage during which fluid may be rapidly lost to the storage medium.

The development of commercially viable, rapid and specific bacterial detection techniques has been worked on world-wide by many companies, often with the ultimate aim of producing an instant 'dip stick' type of test which would specifically detect very low numbers of bacteria, e.g. *Salmonella spp* and which would be stable enough to be stored without significant loss of effectivess. The present invention is a test of this type, eliminating the need for lengthy enrichment stages and is able to rapidly detect very low amounts of antigenic material, such as specific microorganisms. The method can also be developed to any antibody/antigen assay systems, particularly where binding components are able to be fixed to a surface, wherein it can provide high sensitivity detection.

A sensitive and rapid bioluminescent ATP based detection system for bacterial pathogens is the subject of the applicant's copending application No PCT/GB93/01989. The existing patented method relies on the specific release of bacterial ATP by a bacteriophage and its subsequent detection by measuring the light produced after the addition of luciferin and luciferase. However this technique is limited by the amount of ATP present in viable bacterial cells, the sensitivity of the luciferin/luciferase detection system being about 1 pg, equivalent to about 1000 'average' bacterial cells.

Thus in a first aspect, the present invention provides a method of labelling a biological material comprising microencapsulating a nucleotide in microcapsules substantially impermeable to the nucleotide and linking the resulting microcapsules to the bioloigcal material. Preferably the nucleotide is an adenine nucleotide eg. ATP and is in crystalline form. By encapsulating the nucleotide in this form, very high quantities of ATP can be stored, thereby allowing highly sensitive detection eg. of bacteria. Additionally, the use of crystals (as opposed to solutions) gives labels which are inherently more resistent to loss of activity.

The microencapsulation is preferably in a stable material that is inert with respect to the nucleotide; for example a plastics material eg. for ATP, styrene maleic anhydride copolymer may be used. The use of impermeable plastics materials such as those disclosed herein gives labels which are highly resistant to egress of nucleotide. Preferably the copolymer has a styrene/maleic anhydride ratio of at least 3/1, which is particularly effective.

The microcapsules formed are linked to specific antibodies for the antigenic material to be detected, eg. to bacteria specific antibodies. It has been found that spherical bodies of between 1 and 10 μm are convenient for such encapsulated ATP to be effective as a label, but no particular limits are ascribed as routine screening will yield optimal size and form.

Methods for antibody or antigen attachment are well documented in the literature and either passive (adsorption) or covalent coupling may be used; the preferred method being covalent coupling of antibody to the microcapsule surface.

The antibody labelling microcapsules contain a relatively massive amount of ATP, as compared to a bacterial cell, and attach to target antigens on a biological material eg. a bacterium. The biological material itself may be specifically trapped on a surface coated with an antibody specific for that material eg. raised to the target antigen, or another distinguishing antigen. Such surface will typically be on a antibody treated latex bead, magnetic bead or microtitre plate.

In a second aspect of the invention there is disclosed a specific binding agent characterised in that it is labelled by being attached to a microcapsule containing a nucleotide and being substantially impermeable to the nucleotide.

It will be realised that any specific binding agent, not just antibodies and antigens, may be labelled by the method of the present invention. For example agents such as nucleic acid hybridization probes and PCR primers may also be labelled by covalent coupling, eg. through amino-linkers, to microencapsulated nucleotide, particularly ATP.

In a third aspect of the invention there is disclosed a method of performing a specific binding assay comprising the use of a specific binding agent as described hereinbefore. Preferably the assay is targeted at an antigenic material, wherein a solid surface is coated with a capture antibody specific for the targeted material, exposed to a sample suspected of containing the targeted material, exposed to a solution containing an antibody labelled with microencapsulated nucleotide that is specific to the targeted material, unbound antibody removed, the microencapsulated nucleotide released, and the amount of released nucleotide determined and related to the presence of targeted material.

In a fourth aspect of the invention there is provided a test kit suitable for use in performing specific binding assays or in identifying materials to which a specific binding agent will bind specifically characterised in that it comprises a specific binding agent that is labelled as described hereinbefore, optionally with other materials suitable for use in the methods described herein.

Thus in one preferred method of the present invention, target antigenic material (eg. comprising bacteria) is trapped by association with a capture antibody specific for it that has been immobilised upon a solid surface such as a latex bead or a microtitre plate. The plate or bead is washed and exposed to a second antibody labelled with nucleotide, eg. microencapsulated ATP, and, after further washing to remove labelled antibody that has not bound to any captured target antigen, the microcapsules are disrupted to release the nucleotide for subsequently measurement and relation to antigen quantity.

In one particularly advantageous embodiment, the method is employed using antibody-coated magnetic beads, such as Dynabeads (Dynal, UK), to capture bacteria from a sample. The beads are then washed to remove unbound sample, and are then exposed to plastic microcapsules containing nucleotide eg. ATP. After further washing, the bound microcapsules are disrupted to release the ATP for subsequent measurement.

To make most effective use of the advantages of the ATP label it is preferred to measure this rapidly using luciferase/luciferin as is known in the art using a luminometer, with the amount of light derived therefrom being related to the amount of ATP bound to the solid surface, and thus to the amount of captured antigenic material, eg. bacteria. Such relationship is conveniently interpreted by reference to calibration curves constructed by releasing a known amount of ATP from a known amount of microcapsules, or by performing the assay with known amounts of target antigenic material, eg. bacteria.

Methods for disruption of microencapsules will occur to those skilled in the art. Styrene maleic anhydride copolymer microcapsules may be disrupted by a variety of means e.g. alkaline pH or solvents such as methylene chloride, chloroform, carbon tetrachloride, dimethyl formamide, methylethyl ketone, diisopropyl ketone, dioxane, cyclohexanone, tetrahydrofurfuryl alcohol, ethyl acetate and cyclohexane. Acetone is a preferred reagent for the present method, particularly in the form of a 90% aqueous solution.

Using the method of the present invention it is possible to specifically associate relatively large amounts of nucleotide with antigenic materials, particularly large bodies such as bacterial cells, and use this to detect them in very low numbers, preferably in the order of 10–100 cells. This level is well below the commonly accepted detection threshold of $10^5$ cells, and provides the prospect of rapid and direct detection of bacteria from a food material.

The applicant has estimated that a 5 µm diameter polystyrene copolymer microcapsule, assuming a 50% loading, would contain approximately 30 pg of micronised ATP/sphere. This is equivalent to the amount of ATP contained in $3 \times 10^4$ 'average' bacterial cells. It is theoretically possible to encapsulate and measure any nucleotide which may be released from a capsule at the end of the test procedure, for example NAD, NADP, NADH, NADPH, ATP or ADP, cAMP or cGMP, with sensitivity provided by use one or more of the many enzyme based assay systems, e.g. cascade systems, that are available in the art. For example, GB 2213261 discloses a method which may be used with the salicylate monooxygenase system, while other enzyme systems such as the alkaline phosphatase (EC 3.1.3.1.)/NAD/NADP system as disclosed in GB 2240845. Suitable assay systems for ADP, cAMP, cGMP etc. will occur to those skilled in the art.

However, particularly preferred is the measurement of adenosine triphosphate (ATP), that being readily measurable by assay with a variety of enzyme/enzyme substrate combinations by virtue of its being a cofactor in numerous substrate conversions. For the rapid and efficient determination of levels of released ATP in the present application it is especially preferred to utilise enzymes which result in the production of luminescence, most conveniently using luciferase.

ATP can be quantified with commercially available reagents using the process of bioluminescence wherein it is used to drive the reaction in which luciferase catalyses the oxidation of luciferin resulting in the emission of light. The quantum efficiency of this reaction is extremely high and the amount of light produced gives a measure of the quantity of ATP originally present.

The methods and labels of the present invention will now be exemplified by way of illustration only by reference to the following non-limiting example. The great variety of options falling within the scope of the invention will be readily determinable by those skilled in the art on consideration of the general method described above and particularised below.

EXAMPLE

Protocol for Detection of Low Levels of Salmonella in Liquid Media by ATP Bioluminescence a. Strain used: The strain of bacterium to be detected was *Salmonella dublin* (ATCC 15480). Prior to investigations stock cultures were maintained on Brain Heart Infusion (B.H.I.) agar (Unipath Ltd., Basingstoke, Hampshire U.K.) slants at 40° C.

b. Antibody: The antibody used to covalently label the ATP containing microcapsules was a monoclonal antibody to flagella antigens of *Salmonella dublin* purchased from The Central Veterinary Laboratory, Weybridge U.K.

c. Adenosine-5'-triphosohate: ATP disodium salt (A 7699) was purchased from Sigma Chemical Company Ltd., Poole, Dorset U.K. Brain Heart Infusion Broth (BHI)—Unipath Ltd. was used to grow the inoculum. Serial dilutions of broth culture were made using 0.1M potassium phosphate buffer (pH 7).

A suitable kit for detection of this Salmonella using the method of the present invention was provided comprising (a) ATP containing polystyrene beads covalently labelled with anti Salmonella antibodies. (b) Microtitre plates with well surfaces covalently bound with anti—Salmonella antibody. (c) Luciferin/luciferase reagents (e.g. As below).

The spectrophotometer used was model CE 202 (Cecil Instruments, Cambridge, U.K.) with 1 cm. Disposable cuvettes (Whatman International Ltd., Maidstone, U.K.).

Light measurements were made using a luminometer, model LB953 Autolumat (Berthold Instruments U.K. Ltd., St. Albans Hertfordshire), and disposable polystyrene tubes (catalogue number 55.476; Sarstedt, Beaumont Leys, Leicester, U.K.). Light intensity was measured as counts/second (CPS).

The ATP (adenosine-5'-triphosphate) assay mix containing luciferin/luciferase (FL-AAM) and adenosine 5'-triphosphate assay mix dilution buffer (FL-AAB) were obtained from Sigma Chemical Company Ltd., Poole, Dorset U.K. Luciferin/luciferase reagent was diluted 1:25 with the dilution buffer when required.

i) Preparation of styrene maleic anhydride copolymer microspheres containing sodium salt of adenosine triphosphate.

One gram of styrene maleic anhydride copolymer (Elf Atochem SMA 3000—styrene/maleic anhydride copolymer with a styrene/maleic anhydride ratio of 3/1) was dissolved in 5 ml of acetone at 25° C. 500 mg of micronised adenosine triphosphate (ATP) of 2–8 µm particle size was added to the polymer solution with agitation to produce a homogeneous suspension. The resultant suspension was poured into 150 ml of heavy liquid paraffin which was agitated and maintained at 4° C. The liquid paraffin contained 300 µl of sorbitan trioleate as the emulsifying agent. The rate of agitation of the system was adjusted to produce the required droplet size (10–20 µm) of the polymeric dispersion. The temperature of the system was gradually raised to 35° C. over a one hour period and maintained for 4 hours to evaporate the acetone. Once the acetone had evaporated, 100 ml of n-hexane was added to the system which was the allowed to cool to room temperature (25° C.) and agitated for a further 30 minutes. The agitation was stopped and the microspheres were allowed settle to the bottom of the vessel. Most of the liquid paraffin was decanted and the microspheres were vacuum filtered, washed with n-hexane and air dried.

Stability of the ATP-containing 3/1 styrene maleic anhydride copolymer microspheres was confirmed as follows. 50 mg of the microspheres were suspended in 1 ml of phosphate buffered saline (PBS) in microcentrifuge tubes. No swelling was observed. At 1 hour intervals the tubes were centrifuged at 2000g for 5 minutes and the PBS was removed from the tubes and analysed to see how much ATP had been lost into solution from the microspheres. The microspheres were then resuspended in fresh PBS and the process was repeated at 1 hourly intervals for 6 hours. Typical results are shown below, along with the average values for control (i.e. no microspheres) and disrupted microspheres:

| Time (hrs) | ATP (CPS) |
| --- | --- |
| control | ~$10^2$ |
| 1 | $5.4 \times 10^{-3}$ |
| 2 | $4.8 \times 10^{-3}$ |
| 3 | $3.9 \times 10^{-3}$ |
| 4 | $3.8 \times 10^{-3}$ |
| 5 | $4.2 \times 10^{-3}$ |
| 6 | $3.7 \times 10^{-3}$ |
| disrupted | ~$8 \times 10^6$ |

Microspheres/microcapsules of ATP/sodium salt of ATP may also be produced by spray drying a suspension of the said compounds in a suitable polymer solution. Preferred polymers are those which posses excellent antibody binding properties coupled with chemical and water resistance. Examples of suitable polymers are as follows:— methacrylate, polyvinyltoluene, Polystyrene, polymethylstyrene/butadiene styrene/divinylbenzene, and styrene copolymers e.g. styrene maleic anhydride.

ii) Protocol for linking antibodies to microspheres.

Dry microspheres were suspended in PBS buffer (pH 7.4) and left in a blood tube rotator (Stuart Scientific SB1) for 1 hour at 40 rpm at room temperature. To activate the surface of the spheres EDC [1-ethyl 3(3-dimethylaminopropyl) carbodiimide] and N-hydroxysuccinimide were added to the suspension (both approx. 5% by weight of the spheres) and left at room temperature for about 30 minutes. The activated spheres were then centrifuged at 1300 rpm (MSE Micro Centaur centrifuge) for 2 minutes, the buffer discarded, and were washed twice in PBS buffer (to remove any unreacted EDC/NHS), centrifuged at 1300 rpm and the buffer discarded. An appropriate dilution of antibody in PBS buffer was added to the activated beads which were then placed in the blood tube rotator overnight at 40 rpm at room temperature, 25° C. The antibody linked spheres were then centrifuged at 1300 rpm, the buffer removed, then washed 5 times in PBS-buffer (pH 7.4) and finally resuspended in PBS-buffer and stored at 4° C. until used.

iii) Preparation of inoculum.

A broth culture of Salmonella dublin was set up in 10 ml B.H.I. broth and incubated at 37° C. until visibly turbid. The absorbance at 650 nanometeres was measured, and simultaneously a tenfold dilution series from 100 through to $10^{-10}$ was prepared in potassium phosphate buffer. From each dilution of culture five 1 ml. Samples were inoculated with fresh 9 ml. Volumes of B.H.I. broth. These tubes were then incubated overnight at 37° C., and observed for turbidity. From published tables ("Theory and Practice in Experimental Microbiology", G. Meynell & Elinor Meynell, Cambridge University Press) it was possible to determine which cultures contained approximately 100 cells/ml.

iv) Detection of Salmonella dublin

Dilutions of *Salmonella dublin* containing approximately 1, 10,100 and 1000 cells in 200 μl were prepared in phosphate buffered saline and added to wells in a microtitre plate previously coated with anti *Salmonella dublin* antibody and incubated at 4° C. for one hour. The saline was removed from the wells and 100 μl of a suspension of the antibody coated ATP containing beads was added and incubated at 25° C. for 30 minutes.

The wells were gently washed 4 times with distilled water to remove excess unattached beads, the last wash being removed as completely as possible. 50 μl of 90% acetone in distilled water was added to each well and left for 5 minutes to dissolve the microcapsules. Before the acetone had evaporated 250 μl of distilled water was added to dissolve ATP in the aqueous phase. 50 μl volumes were removed from the wells and placed in luminometer tubes. Light measurement was then commenced with 50 μl luciferin/luciferase reagent added to each tube and light output immediately monitored over a 10 second period. Measurements were then plotted as peak light intensity against cell numbers.

Using this protocol a peak count of 40,000 CPS was obtained with wells containing 1,000 cells, 6,000 CPS with wells containing 100 cells, 2,500 CPS with 10 cells and 500 CPS with 1 and zero cells.

v) Storage of labelled microspheres

The long term storage and binding ability of the microspheres was demonstrated as follows: 500 mg amounts of antibody labelled microspheres were stored in dry form in centrifuge tubes at 4° C. for up to 8 months. At approximately monthly intervals 20 mg amounts were assayed for ATP content and binding ability for *Salmonella dublin* cells. Binding ability was subjectively measured by mixing approximately 1 mg of the beads with 50 μl of a culture of *Salmonella dublin* containing $10^6$ cells/ml, placing the drop on a slide under a coverslip and observing at 400x magnification under phase contrast. A positive result would be shown by bacterial cells rapidly adhering to bead surfaces. For the measurement of the ATP content of the beads, approximately 10 mg of the beadswere dissolved in 500 μl of 90% acetone in water. 50 μl volumes were removed and added to a 250 μl volume of distilled water. 50 μl volumes of this dilution were removed and measured for ATP content in a Berthold LB953 Luminometer. The results were as shown in the following table:

| Month | AW (CPS) | Binding ability |
|---|---|---|
| 1 | $8.6 \times 10^8$ | + |
| 2 | $8.2 \times 10^8$ | + |
| 3 | $7.9 \times 10^8$ | + |
| 4 | $8.4 \times 10^8$ | + |
| 6 | $7.8 \times 10^8$ | + |
| 7 | $7.9 \times 10^8$ | + |
| 8 | $8.0 \times 10^8$ | + |

As can be seen, over the course of the measuring period no significant loss of ATP or binding ability was observed.

I claim:

1. A method of labelling a biological material comprising
   (a) microencapsulating a nucleotide in non-liposome microcapsules substantially impermeable to the nucleotide, and
   (b) linking the resulting microcapsules to the biological material.

2. A method as claimed in claim 1 wherein the nucleotide is microencapsulated in crystalline form.

3. A method as claimed in claim 1 wherein the microencapsulation is within a stable material that is inert with respect to the nucleotide.

4. A method as claimed in claim 3 wherein the stable material is a plastics material.

5. A method as claimed in claim 4 wherein the nucleotide is encapsulated within polystyrene, polymethylmethacrylate, polyvinyltoluene, styrene/butadiene or styrene maleic anhydride copolymer.

6. A method as claimed in claim 1 wherein the microencapsulation produces a microcapsule of between 1 and 10 µm diameter containing the nucleotide.

7. A method as claimed in claim 1 wherein the nucleotide is an adenine nucleotide.

8. A method as claimed in claim 7 wherein the adenine nucleotide is adenosine-5'-triphosphate (ATP).

9. A method as claimed in claim 1 wherein the microcapsules formed are linked to a specific binding agent for a target material.

10. A method as claimed in claim 9 wherein the microcapsules are linked to the specific binding agent by covalent coupling.

11. A method as claimed in claim 9 wherein the target material is an antigenic material and the specific binding agent is an antibody.

12. A method as claimed in claim 11 wherein the antigenic material is a microorganism.

13. A specific binding agent labelled by being attached to a non-liposome microcapsule containing a nucleotide and wherein the microcapsule is substantially impermeable to the nucleotide.

14. An agent as claimed in claim 13 wherein the microcapsule contains crystalline nucleotide.

15. An agent as claimed in claim 13 wherein the microencapsulation is within a stable material that is inert with respect to the nucleotide.

16. An agent as claimed in claim 15 wherein the stable material is a plastics material.

17. An agent as claimed in claim 16 wherein the nucleotide is encapsulated within polystyrene, polymethylmethacrylate, polyvinyltoluene, styrene/butadiene or styrene maleic anhydride copolymer.

18. An agent as claimed in claim 13 wherein the agent is an antibody, an antigen, a nucleic acid hybridisation probe or a PCR primer.

19. A method for performing a specific binding assay characterised in that the method comprises at least one step employing a specific binding agent as claimed in claim 13.

20. A method as claimed in claim 19 wherein the assay is targeted at an antigenic material, wherein a solid surface is coated with a capture antibody specific for the targeted material, exposed to a sample suspected of containing the targeted material, exposed to a solution containing the specific binding agent specific to the targeted material, unbound agent is removed, the microencapsulated nucleotide released, and the amount of released nucleotide determined and related to the presence of targeted material.

21. A method as claimed in claim 19 wherein the targeted material comprises a microorganism.

22. A method as claimed in claim 20 wherein the solid surface is a latex bead, a microtitre plate, or a magnetic bead.

23. A method as claimed in claim 19 wherein the microencapsulated nucleotide is released by exposure of the labelled specific binding agent to alkaline pH or a solvent.

24. A method as claimed in claim 23 wherein the solvent is selected from the group consisting of methylene chloride, chloroform, carbon tetrachloride, dimethyl formamide, methylethyl ketone, diisopropyl ketone, dioxane, cyclohexanone, tetrahydrofurfuryl alcohol, ethyl acetate, cyclohexane and acetone.

25. A method as claimed in claim 24 wherein the microencapsulation is within a styrene maleic anhydride copolymer and a 90% aqueous acetone solution is used as release solvent.

26. A method as claimed in claim 19 wherein the nucleotide is ATP and the amount released is determined by relating the amount of light emitted in the presence of luciferin/luciferase luminometry reagent.

27. A test kit suitable for use in performing specific binding assays or in identifying materials to which a specific binding agent will bind specifically, wherein the test kit comprises a specific binding agent that is labeled by being attached to a non-liposome microcapsule, wherein the non-liposome microcapsule contains a nucleotide and is substantially impermeable to the nucleotide.

* * * * *